United States Patent [19]
Tsuji

[11] Patent Number: 5,291,010
[45] Date of Patent: Mar. 1, 1994

[54] SOLID STATE IMAGING DEVICE HAVING A CHAMBERED IMAGING CHIP CORNER

[75] Inventor: Kiyoshi Tsuji, Musashino, Japan

[73] Assignee: Olympus Optical Co., Ltd., Tokyo, Japan

[21] Appl. No.: 770,274

[22] Filed: Oct. 3, 1991

[30] Foreign Application Priority Data

Oct. 4, 1990 [JP] Japan ................... 2-268138

[51] Int. Cl.⁵ ............................. H01J 40/14
[52] U.S. Cl. ................... 250/208.1; 128/6; 257/433; 348/65
[58] Field of Search ............ 250/208.1, 208.5; 358/98, 229, 213.11; 128/6; 257/433

[56] References Cited

U.S. PATENT DOCUMENTS 4,760,440  7/1988  Bigler et al. .
4,868,644  9/1989  Yabe et al. ................ 128/6

FOREIGN PATENT DOCUMENTS

62-16683  1/1987  Japan .
62-94650  6/1987  Japan .

Primary Examiner—David C. Nelms
Assistant Examiner—Que T. Le
Attorney, Agent, or Firm—Armstrong, Westerman, Hattori, McLeland & Naughton

[57] ABSTRACT

This invention is a solid state imaging device provided with an imaging chip having an imaging area and a package enclosing this imaging chip wherein, among a plurality of corners of the image area on the imaging chip, a plurality of corners of the imaging chip and a plurality of corners of the above mentioned package, at least one corner in each corresponding position is chamfered. The chamfered corner of the image area is a region not required to display pictures and does not reduce the displaying performance. In the electronic endoscope, the above mentioned solid state imaging device is arranged within the small area of the insertable section with the chamfered corner directed to the outside.

25 Claims, 7 Drawing Sheets

SOLID STATE IMAGING DEVICE HAVING A CHAMBERED IMAGING CHIP CORNER

BACKGROUND OF THE INVENTION

1. Field of the Invention

This invention relates to a solid state imaging device wherein the corners including the image area of an imaging chip are chamfered and an electronic endoscope provided with the above mentioned solid state imaging device.

2. Related Art And Prior Art Statement

Figure 1:
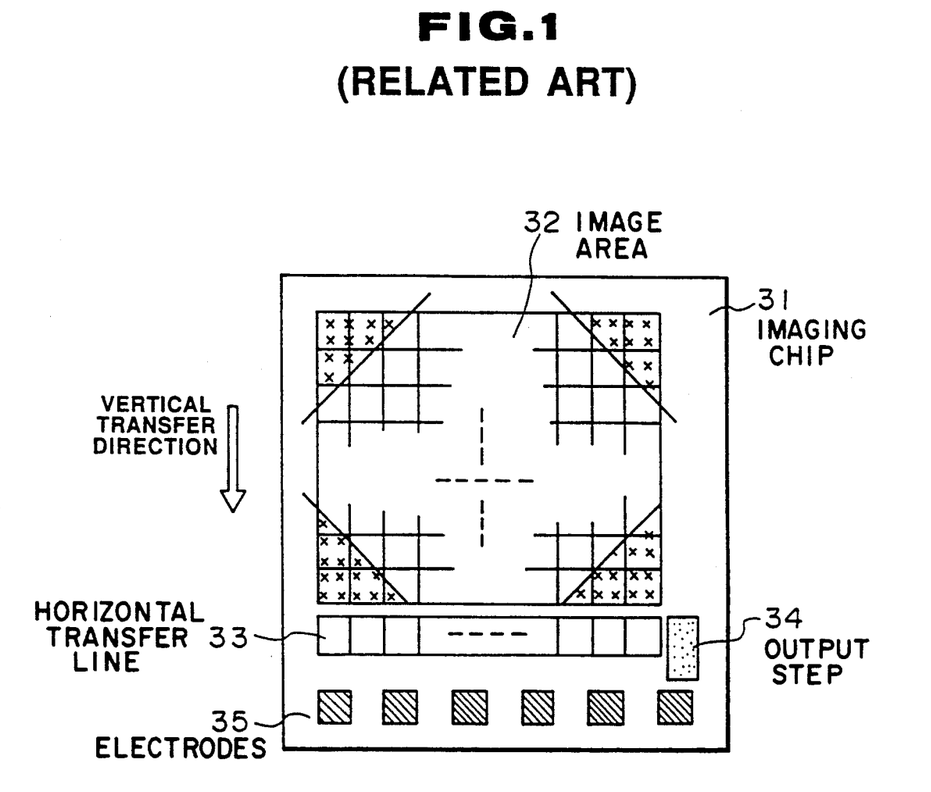
FIG. 1 is a plan view of an imaging chip of a related art.

The imaging chip of a conventional solid state imaging device, for example, in a CCD is generally formed as shown in FIG. 1. An imaging chip 31 comprises an image area 32 consisting of a photodiode and vertical transfer lines, a horizontal transfer line 33 receiving electric charges from the final steps of the above mentioned vertical transfer lines, an output step 34 receiving an electric charge from the final step of this horizontal transfer line 33 and outputting it and electrodes 35 for transmitting and receiving signals and power sources for these respective parts. The above mentioned image area 32 is formed to be like a rectangle corresponding to the aspect ratio of a television displayed picture.

Figure 2A:
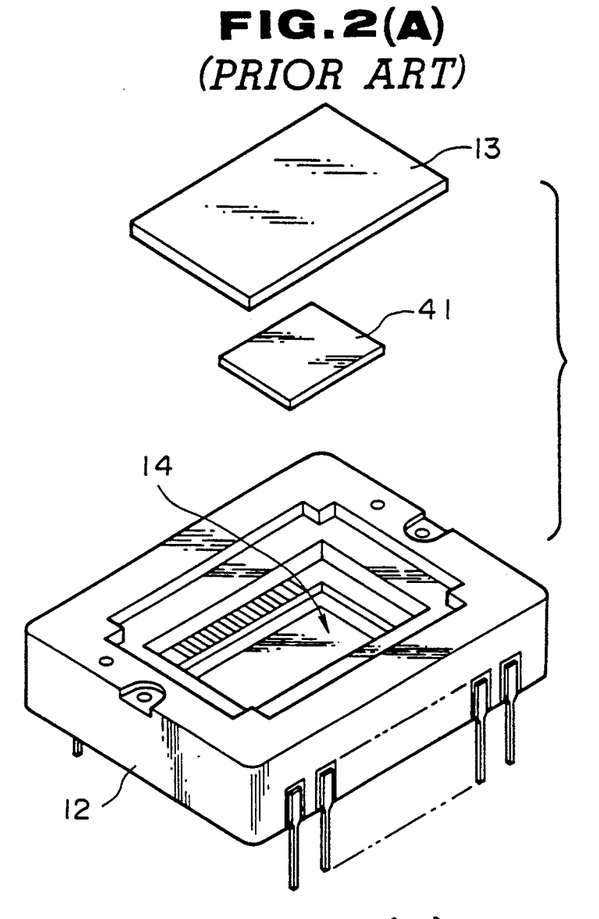
FIG. 2(A) is a disassembled perspective view of a solid state imaging device as an example of a prior art.
Figure 2B:
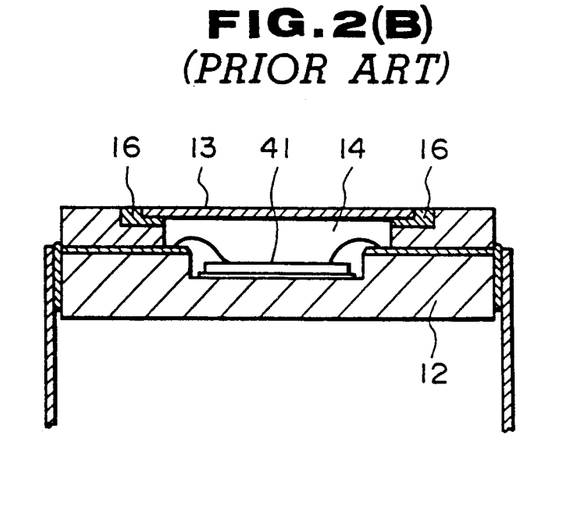
FIG. 2(B) is a sectioned view of FIG. 2(A).
Figure 3:
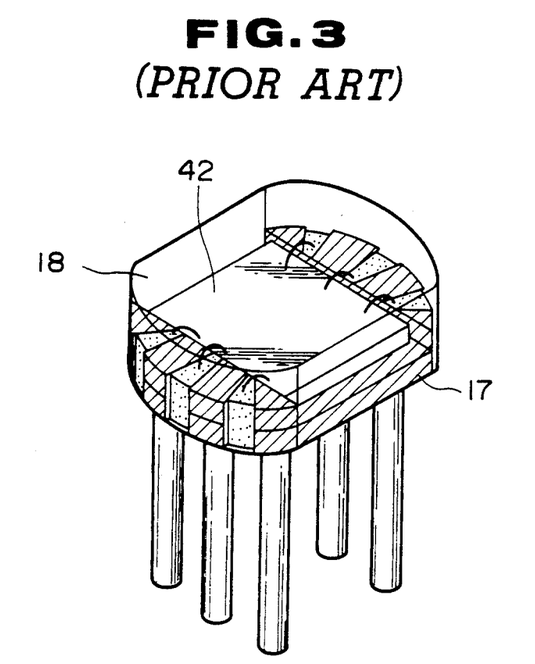
FIG. 3 is a perspective view of a solid state imaging device of another prior art.

The above mentioned imaging chip is composed of silicon and is therefore enclosed within a package to improve the durability to the humidity and external force. As an example of a solid state imaging device enclosing the above mentioned imaging chip, there is such solid state imaging device enclosing an imaging chip in a ceramic package as is disclosed in the publication of Japanese Utility Model Application Laid Open No. 94650/1987 and shown in FIGS. 2(A) and 2(B). This imaging chip 41 is housed in an imaging chip housing recess 14 on a ceramic substrate 12 and is air-tightly sealed with a sealing glass 13 through a resin 16. As an example of making the package small, there is such solid state imaging device resin-sealing an imaging chip 42 with a transparent resin as is disclosed in Japanese Patent Application Laid Open No. 16683/1987 and shown in FIG. 3 and this imaging chip 42 is fixed and arranged on the package 17 and is resin-sealed with a transparent resin.

Figure 5:
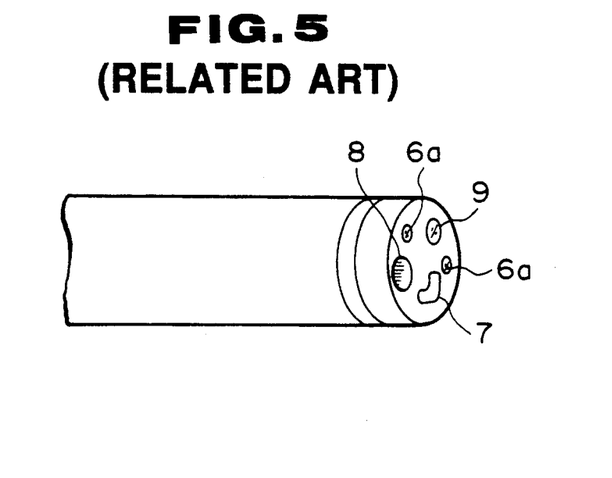
FIG. 5 is a perspective view of an electronic endoscope tip part of a related art.

Now, an electronic endoscope has the above mentioned solid state imaging device arranged within an insertable section tip shown in FIG. 5 to be inserted into a body cavity or the like for observation and required to be fine in the diameter. This electronic endoscope is provided at the insertable section tip with a light guide emitting window 6a, an air and water feeding nozzle 7, a forceps channel 8 and an objective lens 9 as shown, for example, in FIGS. 5 and 6. A solid state imaging device 11 shown by the two-point chain line in FIG. 6 is arranged on the inner side of this objective lens 9.

Figure 6:
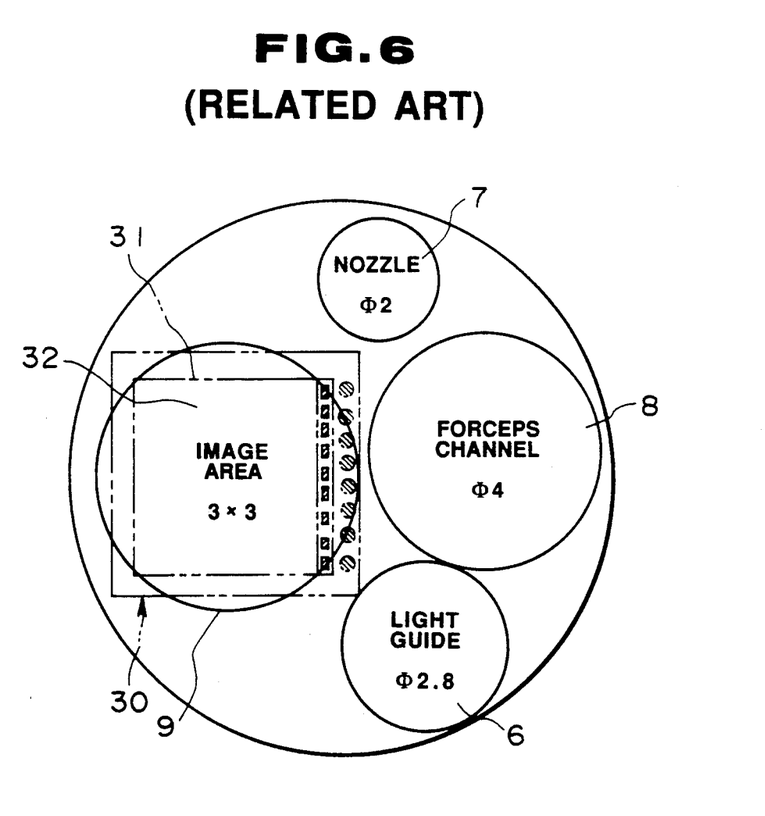
FIG. 6 is a sectioned explanatory view of a solid state imaging device of a related art as arranged in an electronic endoscope tip part.

If the above mentioned respective components are arranged so that the outside diameter of the tip part of the above mentioned electronic endoscope may be as fine as possible, they will be as shown in FIG. 6. If the respective outside diameters of the above mentioned respective components are set so that, for example, the diameter of the light guide 6 may be about 2.8 Mm, the diameter of the air and water feeding nozzle 7 may be about 2 mm, the diameter of the forceps channel 8 may be about 4 mm and further the image area 32 of the solid state imaging device 30 is set to be, for example, 3×3 Mm, the outside diameter of the above mentioned endoscope tip part will be about 9.1 Mm at the minimum.

Figure 4:
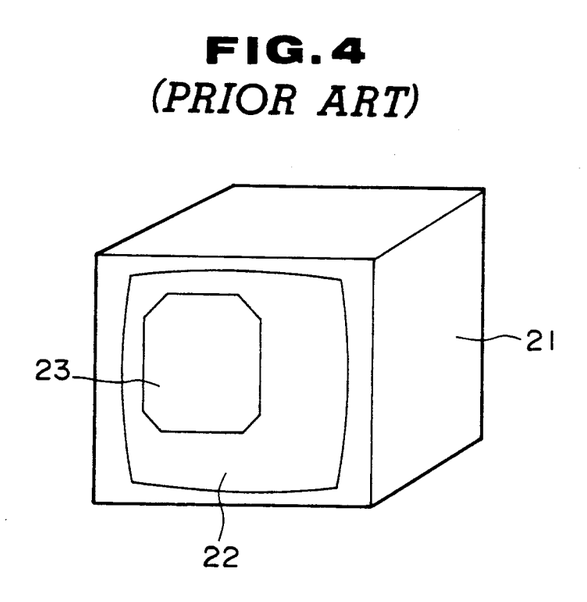
FIG. 4 is an explanatory view of a displaying monitor of an electronic endoscope of a prior art.

On the other hand, as the image area 2 corresponding to the peripheral part of the above mentioned objective lens 9 lacks the incident light amount, the displayed picture of the above mentioned endoscope will become dark in the four corners. Also, by the characteristics of the lens, the resolution will reduce. In order to cope with this fact, as shown in FIG. 4, on the picture 22 of the endoscope image displaying monitor 21, the endoscope image displaying area 23 is chamfered in the four corners so as to be octagonal. This shows that, in the conventional purely optical medical endoscope, as the observing area shape is circular, even in the electronic endoscope, the shape of the displayed picture need not always be square and is well usable.

In case the area of the imaging surface of the above mentioned solid state imaging device is to be made as small as possible, it will be restricted by the contour dimension of the imaging chip. Also, the shape of the above mentioned imaging surface will be restricted by the shape of the above mentioned imaging chip and will therefore become rectangular. Further, in the case of the above mentioned electronic endoscope as an example of an instrument having a solid state imaging device built-in, in order to reduce the pain of the patient when the endoscope is inserted into the body cavity, it is preferable that the outside diameter of the tip part is as fine as possible but, if the outside diameter of the light guide is made fine, the illuminating light amount will decrease and the uniformly illuminatable illumination range will become narrow. In order that many kinds of forceps may be inserted in response to various medical treatments, it is preferable that the outside diameter of the channel is large. Therefore, in order that an instrument in which a solid state imaging device is arranged may be made small to the extremity, the above mentioned solid state imaging device must be able to be arranged within an area as small as possible.

As described above, in order that the imaging chip may be made small by the requirement of making small the instrument mounted with the above mentioned solid state imaging device, the area of the above mentioned imaging surface must be made small. However, there is a defect that, if the dimension of the above mentioned imaging chip is made small, the resolution and sensitivity will reduce.

OBJECTS AND SUMMARY OF THE INVENTION

An object of the present invention is to provide a solid state imaging device which can be arranged within a small area by well securing the size of the image area and without reducing the displaying performance and by which, as a result, such instrument wherein it is arranged as, for example, an endoscope can be made small or fine in the diameter.

Another object of the present invention is to provide a solid state imaging device whereby the space within the instrument can be effectively utilized by extending the diameter or increasing the number of such components provided in the instrument as, for example, a forceps channel and light guide.

Farther another object of the present invention is to provide an electronic endoscope wherein the insertable section having a solid state imaging device can be made fine in the diameter.

Further another object of the present invention is to provide an electronic endoscope wherein the space within the insertable section can be effectively utilized by extending the diameter or increasing the number, for example, of forceps channels and light guides provided in the insertable section having a solid state imaging device.

Another object of the present invention is to provide a solid state imaging device which can prevent an output image from darkening due to the shortage of incident light in an image area corresponding to a peripheral part of an object lens.

Briefly the present invention is a solid state imaging device which is provided with an imaging chip having an image area imaging an image and a package enclosing this imaging chip and in which at least one corner part of the image area on the above mentioned imaging chip and the corner part corresponding to at least the above mentioned image area of the above mentioned imaging chip are chamfered and the corner part of the above mentioned package corresponding to this imaging chip is also chamfered.

The other features and advantages of the present invention will become apparent enough with the following detailed description.

BRIEF DESCRIPTION OF THE DRAWINGS

FIGS. 7 to 10 relate to the first embodiment of the present invention.

FIGS. 11 and 12 relate to the second embodiment of the present invention.

BEST MODE FOR CARRYING OUT THE INVENTION

Figure 7:
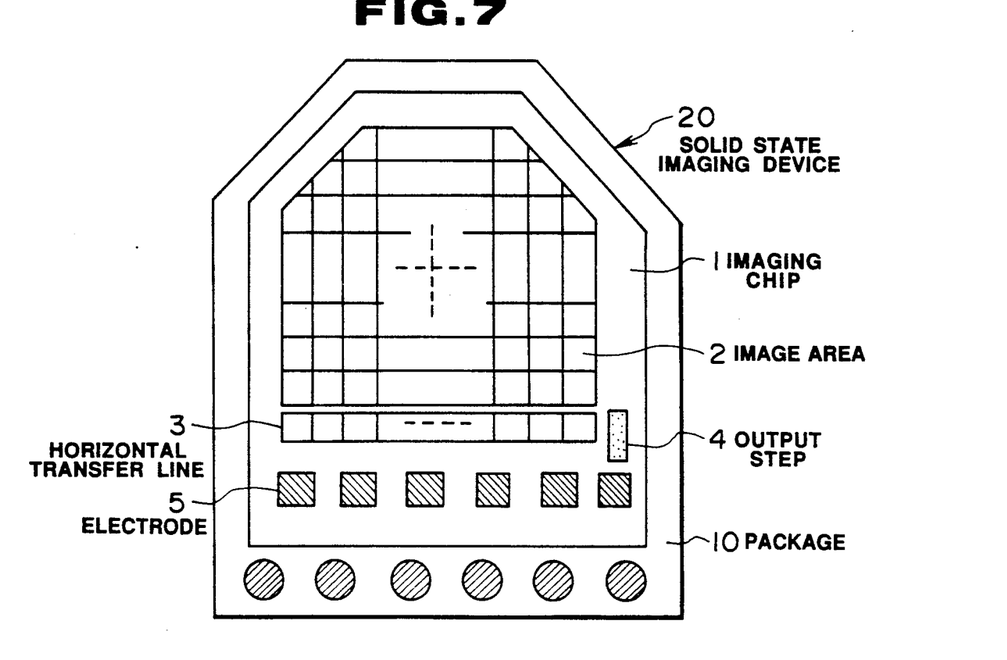
FIG. 7 is an elevation of a solid state imaging device.

An imaging chip 1 of a solid state imaging device 20 shown in FIG. 7 is formed, for example, of a CCD. On this imaging chip 1 is formed an image area 2 comprising a photodiode receiving a light and vertical transfer lines transferring electric charges. A horizontal transfer line 3 receiving electric charges from the final steps of the above mentioned vertical transfer lines is formed in the end part of this image area 2. An output step 4 receiving from the final step of the above mentioned horizontal transfer line 3 the transferred electric charge is formed on the side of this horizontal transfer line 3. An electric charge is output from this output step 4. Electrodes 5 for transmitting and receiving signals and power sources for the above mentioned respective parts are formed in the end part of the above mentioned imaging chip 1. Further, the above mentioned imaging chip 1 is enclosed within a package 10.

As an instrument mounted with the above mentioned solid state imaging device 20, there is an electronic endoscope for observing, for example, a body cavity interior or the like.

Figure 9:
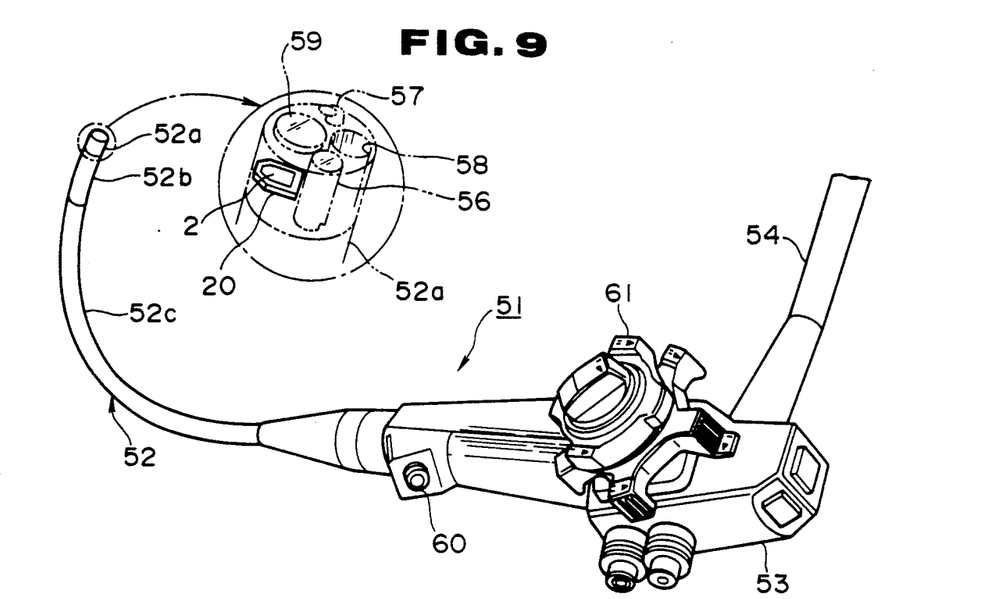
FIG. 9 is a general view of the electronic endoscope.

As shown in FIG. 9, this electronic endoscope 51 is provided with a flexible insertable section 52 to be inserted into an object to be inspected and a thick operating section 53 connected to this insertable section 52 at the rear end. A flexible universal cord 54 is extended sidewise from the above mentioned operating section and is provided at the end with a connector not illustrated which is to be connected to a light source apparatus, video processor and monitor not illustrated.

The above mentioned insertable section 52 comprises a rigid tip part 52a, a bendable part 52b and a flexible part 52b in the order from the tip side.

Also, in FIG. 9 is shown the above mentioned tip part 52a as magnified to be perspective. This tip part 52a is provided with a light guide 56 emitting window 56a, an air and water feeding nozzle 57, a forceps channel port 58 and an objective lens 59.

The above mentioned light guide 56 comprises a fiber bundle, is inserted through the above mentioned insertable section 52, operating section 53 and universal cord 54 and is connected to the above mentioned connector. An illuminating light emitted from a light source lamp not illustrated within the above mentioned light source apparatus is to enter this light guide 56 at the entrance end.

An air and water feeding tube not illustrated is connected to the above mentioned air and water feeding nozzle 57, is inserted through the above mentioned insertable section 52, operating section 53 and universal cord 54 and is connected to the above mentioned connector. Also, the above mentioned forceps channel port 58 is connected through a channel connecting pipe not illustrated to a forceps inserting port 60 provided in the operating section 53.

The above mentioned bendable part 52b is bendable in the vertical/horizontal direction by the operation of an angle operating knob 61 provided on the operating section 53.

Further, inside the above mentioned objective lens 59, the above mentioned solid state imaging device 20 is provided and the image area 2 of this solid state imaging device 20 and the objective lens 59 are arranged as opposed to each other. The above mentioned solid state imaging device 20 converts the observed image coming in through the objective lens 59 to an electric signal which is output to the above mentioned video processor. The above mentioned monitor displays the endoscope observed image.

The entering light amount is so short in the image area 2 corresponding to the peripheral part of the objective lens 59 that the displayed picture of the above mentioned endoscope will be dark in the four corners and will also reduce in the resolution as a characteristic of the lens. Therefore, as shown in FIG. 4, the displayed picture 23 of the above mentioned endoscope is made, for example, octagonal with the four corners chamfered. In this case, the image signals obtained from the four corners of the image area on the imaging chip will be electrically removed at the time of displaying or the image area will be optically masked in the four corners. Thus, depending on the instrument mounted with the solid state imaging device, the four corners of the image area of the solid state imaging device are not always necessary.

Therefore, in this embodiment, two of the four corners of the above mentioned image area 2 are chamfered. The two corners in contact with the above mentioned horizontal transfer line 3 among the corners of this image area 2 can not be chamfered because the above mentioned vertical transfer lines transferring electric charges can not be removed though the above mentioned photodiode structure is not necessary. Therefore, the two corners not in contact with the above mentioned horizontal transfer line 3 among the corners of the above mentioned image area 2 are chamfered. Also, the corners of the above mentioned imaging chip 1 corresponding to them are chamfered. Further, on the package 10 enclosing the chamfered imaging chip 1, two corners corresponding to the chamfers of the imaging chip 1 are chamfered.

Thus, the solid state imaging device 20 including the image area 2 in this embodiment can be changed to be of a polygonal contour from the square contour and can be made small in the area by chamfering the corners. Therefore, this solid state imaging device 20 can be arranged within a small area so as to be able to be arranged in an instrument required to be small or fine in the diameter to meet the requirement. That is to say, as shown in FIG. 8, in case the solid state imaging device 20 in this embodiment is used in the above mentioned electronic endoscope 51, the solid state imaging device 20 will be arranged with the two chamfered corners directed to the outer peripheral side of the tip part 52a of the endoscope.

In case the above mentioned image area 2 is not chamfered, for example, in the corner parts, unless the dimension of the image area is made small, the image area 2 will not be able to be arranged in the fine diameter tip part 52a of the above mentioned endoscope 51. However, the above mentioned image area 2 can be formed to be large in the required dimension, can well secure the displaying performance and can be arranged in the fine diameter tip part 52a of the above mentioned endoscope 51.

Figure 8:
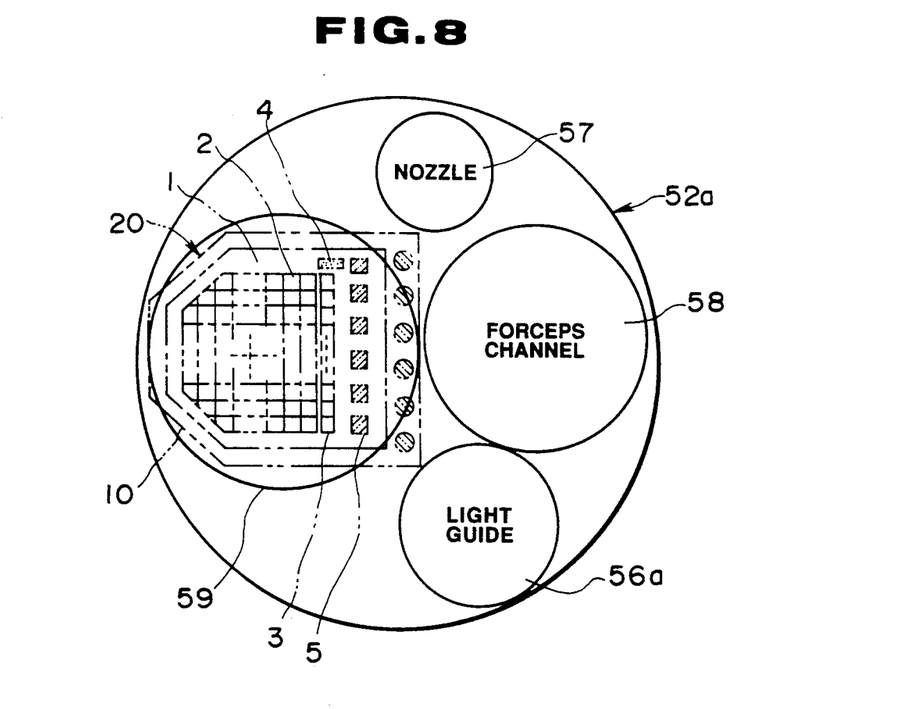
FIG. 8 is an arrangement explaining view of an electronic endoscope provided with a solid state imaging device.
Figure 10:
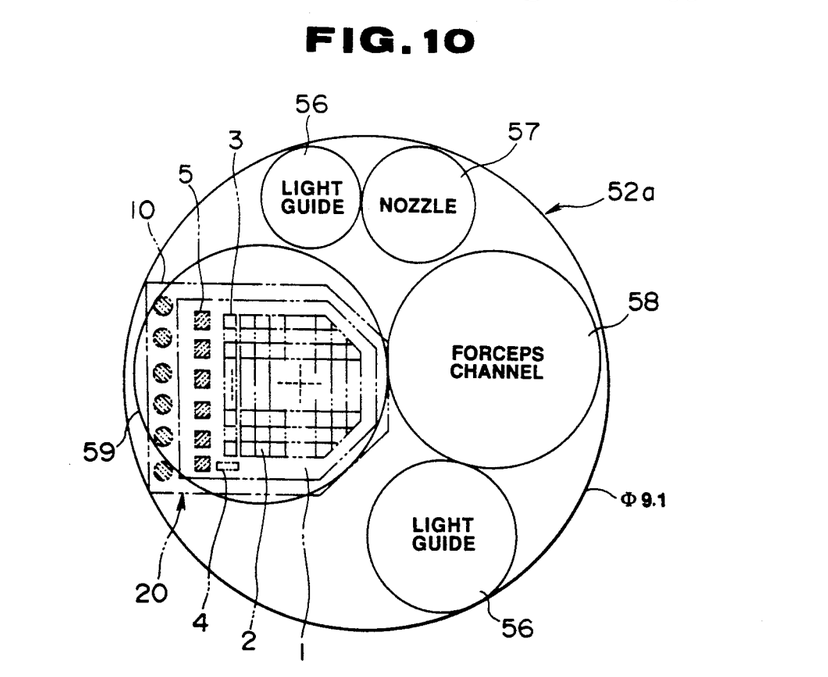
FIG. 10 is an arrangement explaining view different from FIG. 8 of an electronic endoscope provided with a solid state imaging device.

In FIG. 10 as different from FIG. 8, the solid state imaging device 20 is shown to be arranged with the two chamfered corners directed to the inside of the tip part 52a. In the case of this arrangement, inside the endoscope tip part 52a, a space can be made by the two chamfered corner parts of the solid state imaging device 20 and therefore the illuminating light amount can be efficiently fed to the inspected object, for example, with two light guides 56 or the forceps channel 58 and nozzle 57 can be made large in the diameter.

Figure 11:
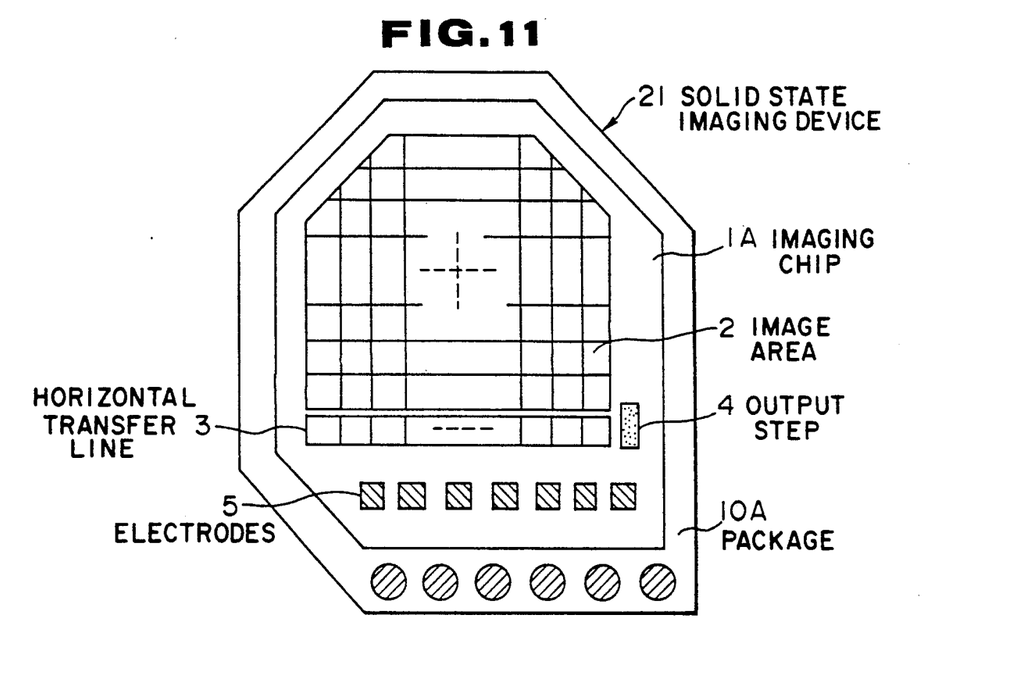
FIG. 11 is an explanatory view of a solid state imaging device.
Figure 12:
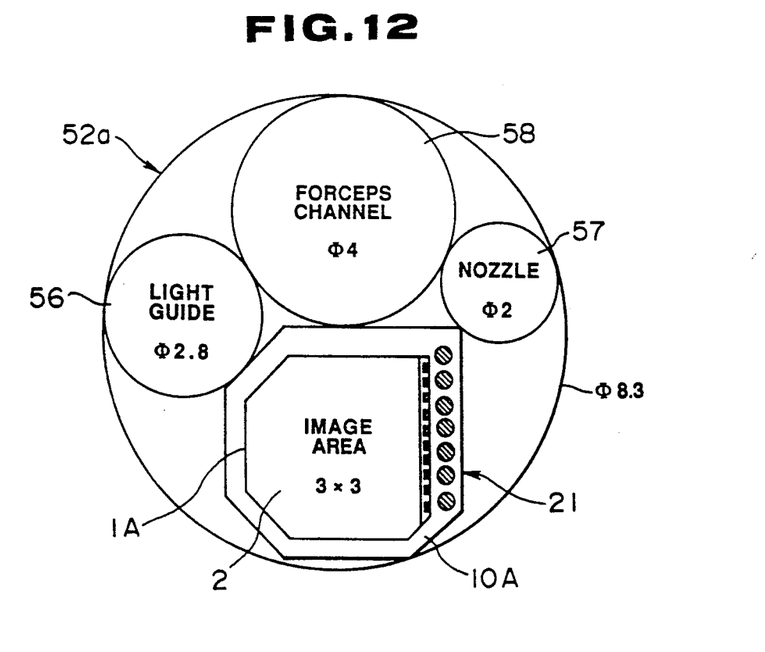
FIG. 12 is a sectioned view of the solid state imaging device as arranged in an electronic endoscope tip part.

FIGS. 11 and 12 relate to the second embodiment of the present invention. FIG. 11 is an explanatory view of a solid state imaging device. FIG. 12 is a sectioned explanatory view of the solid state imaging device of FIG. 11 as arranged in the tip part of an electronic endoscope.

As shown in FIG. 11, the solid state imaging device 21 of this embodiment is chamfered in three corners as against the solid state imaging device 20 of the first embodiment chamfered in two corners.

The imaging chip 1A of the above mentioned solid state imaging device 21 is formed substantially the same as in the first embodiment and is enclosed in a package 10A chamfered in three corners. The other same formations and operations as in the first embodiment shall bear the same reference numerals and shall not be explained here.

In this embodiment, two corners of the image area 2 are chamfered the same as in the first embodiment and, in addition, one of the remaining corners of the above mentioned imaging chip 1A is chamfered. That is to say, in the imaging chip 1A, a total of three corners are chamfered. The electrodes 5 in the above mentioned imaging chip 1A are displaced in the direction of the above mentioned output step 4 and thereby the corner positioned on the horizontal transfer line 3 side opposite the output step 4 is chamfered. Further, the package 10A enclosing the chamfered imaging chip 1A is chamfered in three corners so as to correspond to the chamfers of the imaging chip 1.

FIG. 12 shows the solid state imaging device 21 enclosing the above mentioned imaging chip 1A as arranged in the electronic endoscope tip part 52a. In the tip part 52a of the above mentioned electronic endoscope are arranged the above mentioned solid state imaging device 21, light guide 6, air and water feeding nozzle 7 and forceps channel 8. The above mentioned light guide 6 emits an illuminating light toward the object from the tip and is formed, for example, of an optical fiber bundle. The air and water feeding nozzle 7 feeds air and water to elevate the pressure within the body cavity and wash the objective lens. The forceps channel 8 is to have various forceps inserted through it to make such medical treatments as collecting living body tissues and injecting dyes and medicinal liquids.

If the respective outside diameters of the above mentioned respective components are set, for example, so that the diameter of the light guide 6 may be about 2.8 mm, the diameter of the air and water feeding nozzle 7 may be about 2 mm and the diameter of the forceps channel 8 may be about 4 mm and further the image area 2 of the above mentioned solid state imaging device 21 is set to be, for example, $3 \times 3$ mm, the outside diameter of the above mentioned endoscope tip part will be about 8.3 Mm at the minimum. Therefore, in case the solid state imaging device 21 of this embodiment is arranged in the above mentioned endoscope, the outside diameter of the endoscope tip part will be able to be made smaller by about 10% than in the prior example.

Thus, in the case of arranging a circular component and solid state imaging device within a circular instrument, if the corner parts not always necessary in the above mentioned solid state imaging device 21 are chamfered, the contour of the above mentioned solid state imaging device 21 will be able to be near to a circle, will be able to be arranged within a small area without reducing the displaying performance and will be able to make small the instrument in which the above mentioned solid state imaging device is arranged.

Furthermore, in the endoscope tip part 52a, as one of the three chamfered corners of the solid state imaging device 21 is arranged inside the tip part 52a, a space will be made so that, for example, the light guide 56 may be made large in the diameter or another forceps channel may be arranged.

By the way, the number of the chamfers of the solid state imaging device is not limited to the above mentioned embodiment. Depending on the contour of the instrument in which the solid state imaging device is arranged, the imaging device may be chamfered so that the contour may be optimum to make the device small. If the image area can be chamfered, the imaging chip will not be limited to the CCD.

It is apparent that, in this invention, different working modes can be formed in a wide range on the basis of the spirit of the invention. This invention is not restricted by its specific working mode except being limited by the appended claims.

What is claimed is:

1. A solid state imaging device, comprising:
   an imaging chip having an imaging area for imaging an image and a package for enclosing said imaging chip, wherein at least one corner at a corresponding position in said imaging chip, and said package is chamfered.

2. A solid state imaging device according to claim 1, wherein three corners at corresponding positions of the imaging chip and the package are chamfered.

3. A solid state imaging device according to claim 1, wherein said imaging chip has transfer lines for receiving electric charges from said image area, and wherein said at least one corner at a corresponding position of said imaging chip and said package, which is opposite a side on which said transfer lines are arranged, is chamfered.

4. A solid state imaging device according to claim 1, wherein said solid state imaging device is arranged in an electronic endoscope having an insertable section, and wherein at least one corner of each of said imaging chip and said package which is positioned on the outer peripheral side of the insertable section of said electronic endoscope is chamfered.

5. A solid state imaging device according to claim 1, wherein said solid state imaging device is arranged in an electronic endoscope having an insertable section, and wherein at least one corner of each of said imaging chip and said package, which is positioned inside the insertable section of said electronic endoscope, is chamfered.

6. A solid state imaging device, comprising:
   an imaging chip having an imaging area for imaging an image and a package for enclosing said imaging chip, wherein at least one corner at a corresponding position in the image area on said imaging chip, said imaging chip, and said package is chamfered.

7. A solid state imaging device according to claim 6, wherein three corners at corresponding positions of the image area on said imaging chip, the imaging chip and the package are chamfered.

8. A solid state imaging device according to claim 6, wherein said imaging chip has transfer lines for receiving electric charges from said image area, and
   wherein said at least one corner at a corresponding position of the image area on said imaging chip, said imaging chip and said package, which is opposite a side on which said transfer lines are arranged, is chamfered.

9. A solid state imaging device according to claim 8, wherein said imaging chip has electrodes for inputting and for outputting electric charges received by said transfer lines or for receiving signals from an outside source; and
   wherein said electrodes are located on a side on which non-chamfered corners of said imaging chip and corners of packages are arranged.

10. A solid state imaging device according to claim 8, wherein said imaging chip has electrodes for inputting and for outputting electric charges received by said transfer lines or for receiving signals from an outside source;
    wherein said electrodes are located in non-chamfered corners of said imaging chip and on the side on which a plurality of packages are arranged.

11. A solid state imaging device according to claim 6, wherein said solid state imaging device is arranged in an electronic endoscope having an insertable section, and wherein at least one corner of each of the image area on said imaging chip to be chamfered, said imaging chip and said package which is positioned on the outer peripheral side of the insertable section of said electronic endoscope is chamfered.

12. A solid state imaging device according to claim 6, wherein said solid state imaging device is arranged in an electronic endoscope having an insertable section, and wherein at least one corner of each of the image area on said imaging chip to be chamfered, said imaging chip and said package, which is positioned inside the insertable section of said electronic endoscope, is chamfered.

13. An electronic endoscope having an insertable section tip portion, comprising a solid state imaging device provided with an imaging chip having an image area for imaging an image,
    wherein at least one corner at a corresponding position of each of the image area on said imaging chip of said solid state imaging device and said imaging chip is chamfered to form said solid state imaging device.

14. An electronic endoscope according to claim 13, wherein said solid state imaging device is arranged so that the image area on said imaging chip of said solid state imaging device is parallel with a plane intersecting at right angles with an axial direction of the insertable section of said electronic endoscope.

15. An electronic endoscope according to claim 13, wherein said solid state imaging device is arranged so that at least one of said chamfered corners of the image area on said imaging chip of said solid state imaging device and the imaging chip are along a contour of the insertable section of said electronic endoscope.

16. An electronic endoscope according to claim 13, wherein said solid state imaging device is arranged so that at least one of said chamfered corners of the image area on said imaging chip of said solid state imaging device and the imaging chip are directed to an inside portion of the insertable section of said electronic endoscope and components are arranged adjacent to the corners of said solid state imaging device which are arranged so as to be directed to the inside portion of said insertable section.

17. An electronic endoscope according to claim 13, wherein the imaging chip of said solid state imaging device has a transfer line for receiving an electric charge from said image area, and wherein at least one of said chamfered corners of the image area on said imaging chip and said imaging chip is positioned opposite the side on which said transfer line is arranged in said solid state imaging device.

18. An electronic endoscope according to claim 13, wherein the imaging chip of said solid sate imaging device has an electrode for inputting and for outputting an electronic charge received by said transfer line or for receiving a signal from an outside source, and wherein said solid state imaging device is arranged in the position of said electrode as displaced on the side on which the non-chamfered corners of said imaging chip and corners of said package are arranged.

19. An electronic endoscope according to claim 13, wherein the image area on a non-chamfered imaging chip of said solid state imaging device and components arranged near the corners of the imaging chip have cross-sectioned areas which are smaller than the cross-sectioned areas of the image area on said chamfered imaging chip and the components arranged near the corners of the imaging chip.

20. A solid state imaging device, comprising:

an imaging chip having an imaging area for imaging an image and a package for enclosing said imaging chip, wherein all the corners other than at a corresponding position in the image area on said imaging chip, said imaging chip and said package are chamfered.

21. A solid state imaging device having an insertable section, comprising an imaging chip having an imaging area for imaging an image and a package for enclosing said imaging chip mounted at said insertable section, wherein at least one corner at a corresponding position of each of said imaging chip and said package is chamfered and is arranged at an outer peripheral side of said insertable section.

22. A solid state imaging device having an insertable section, comprising an imaging chip having an imaging area for imaging an image and a package for enclosing said imaging chip mounted at said insertable section, wherein at least one corner at a corresponding position of each of said imaging chip and said package is chamfered and is arranged at an inside portion of said insertable section.

23. A solid state imaging device, comprising an imaging chip having an image area for imaging an image, wherein at least one corner at a corresponding position of each of the image area on said imaging chip of said solid state imaging device and said imaging chip is chamfered to thereby provide a solid state imaging device which can prevent an output image from darkening due to a shortage of incident light in an image area corresponding to a peripheral part of an objective lens.

24. A solid state imaging device according to claim 23, wherein the imaging chip of said solid state imaging device has a transfer line for receiving an electric charge from said image area, and wherein at least one of said chamfered corners of the image area on said imaging chip and said imaging chip is positioned opposite the side on which said transfer line is arranged.

25. A solid state imaging device according to claim 24, wherein the imaging chip of said solid state imaging device has an electrode for inputting and for outputting an electric charge received by said transfer line or for receiving a signal from an outside source, and wherein said electrode is arranged as displaced in the position on the side on which the non-chamfered corners of said imaging chip and corners of said a package are arranged.

* * * * *